United States Patent [19]

Lin et al.

[11] Patent Number: 5,210,195

[45] Date of Patent: May 11, 1993

[54] BIS(2,2',6,6'-TETRAMETHYL-4-AMINOE-THYLENEAMIDOPIPERIDYL) POLYOXYALKYLENE

[75] Inventors: Jiang-Jen Lin, Houston; George P. Speranza, Austin, both of Tex.

[73] Assignee: Texaco Chemical Co., White Plains, N.Y.

[21] Appl. No.: 789,500

[22] Filed: Nov. 8, 1991

[51] Int. Cl.$^5$ .................. C07D 211/28; C07D 211/32
[52] U.S. Cl. .................... 546/190; 546/186; 524/99; 524/103
[58] Field of Search ................ 546/190, 186; 524/99, 524/103

[56] References Cited

U.S. PATENT DOCUMENTS

| | | | |
|---|---|---|---|
| 4,526,972 | 7/1985 | Speranza et al. | 546/191 |
| 4,556,714 | 12/1985 | Karper | 546/190 |
| 4,716,187 | 12/1987 | Ávár | 524/99 |
| 4,725,634 | 2/1988 | Ishii et al. | 524/103 |
| 4,730,017 | 3/1988 | Ávár | 524/103 |
| 4,762,872 | 8/1988 | Lai et al. | 524/100 |
| 4,847,380 | 7/1989 | Speranza et al. | 546/190 |
| 4,921,893 | 5/1990 | Ávár | 524/99 |
| 5,026,749 | 6/1991 | Cantatore et al. | 524/99 |

Primary Examiner—Marianne M. Cintins
Assistant Examiner—Michael B. Hydorn
Attorney, Agent, or Firm—James J. O'Loughlin; Henry H. Gibson

[57] ABSTRACT

Polyoxyalkylene diamines react with excess acrylate to form diesters which react with 2,2',6,6'-tetramethyl-4-aminopiperidines to give a product of formula 1, useful as photostabilizer for photosensitive materials.

Formula 1

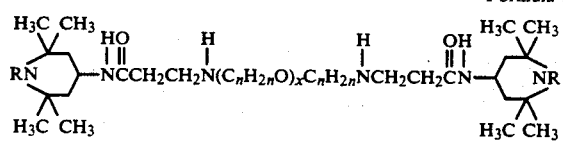

4 Claims, No Drawings

BIS(2,2',6,6'-TETRAMETHYL-4-AMINOETHYLENEAMIDOPIPERIDYL) POLYOXYALKYLENE

BACKGROUND OF THE INVENTION

1. Field of the Invention

This invention concerns new tetramethylaminopiperidine derivatives, and more particularly to products of polyoxyalkylene diamine reacted with alkyl acrylate and further with 2,2',6,6'-tetramethyl-4-aminopiperidine, which are useful as photostabilizers.

2. Description of Related Information

Various synthetic polymers and other materials are light sensitive. When exposed to sunlight or other sources of ultraviolet light, such materials undergo a progressive change in physical properties, typically losing mechanical strength and changing color, resulting in softening, brittleness, discoloration and other undesirable consequences. Photostabilizers have been added to such materials to prevent or diminish their deterioration.

Derivatives of 2,2',6,6'-tetramethyl-4-aminopiperidine (TMAP) have been used as photostabilizers. For example, U.S. Pat. No. 4,526,972 (Speranza et al.) discloses TMAP derivatives made by hydrogenating the product of TMAP reacted with polyoxyalkylene polyamine. U.S. Pat. No. 4,847,380 (Speranza et al.) discloses TMAP derivatives made by reacting polyoxyalkylene diamine or diol with dicarboxylic acid or diisocyanate followed by reaction with TMAP to form TMAP dimer linked to polyoxyalkylene through amide, urea or urethane bonds.

U.S. patent application Ser. No. 07/410,444 (Lin et al.) filed Sep. 20, 1989 discloses reacting alkyl acrylates with a molar excess of polyoxyalkylene polyamine to make polyamidoamines useful as epoxy curing agents, reaction-injection-molding (RIM) chain extenders and other polymer applications.

SUMMARY OF THE INVENTION

This invention concerns photostabilizers represented by the structure set forth in the Formula 1.

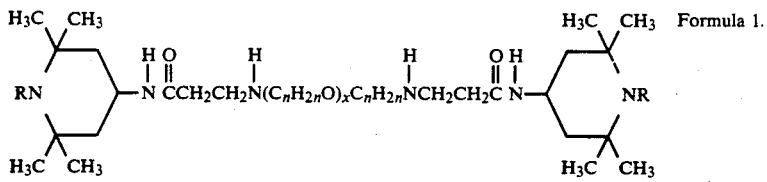

Bis(2,2',6,6'-tetramethyl-4-aminoethyleneamidopiperidyl) Polyoxyalkylenes

In Formula 1, each n is individually 2 or 3, R is hydrogen or hydrocarbyl having from 1 to about 16 carbon atoms and x is from 1 to about 60. Light stabilized compositions comprising an effective light stabilizing amount of such photostabilizer and at least one photosensitive material are provided. Processes for producing such photostabilizers by (1) reacting polyoxyalkylene diamine with a molar excess of alkyl acrylate to produce bis(alkylcarboxylatoethyleneamino) polyoxyalkylene intermediate; and (2) reacting the intermediate with TMAP compound which is unsubstituted or N-alkyl substituted, 2,2',6,6'-tetramethyl-4-aminopiperidine.

DETAILED DESCRIPTION OF THE INVENTION

The bis (2,2',6,6'-tetramethyl-4-aminoethyleneamidopiperidyl) polyoxyalkylene of this invention can be made in two steps. In the first step, polyoxyalkylene diamine reacts with alkyl acrylate, through Michael addition, to produce bis(alkylcarboxylatoethyleneamino) polyoxyalkylene intermediate. This addition reaction is shown in Equation 1.

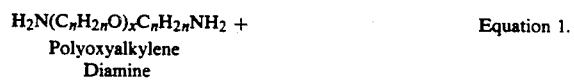

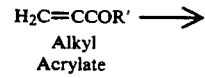

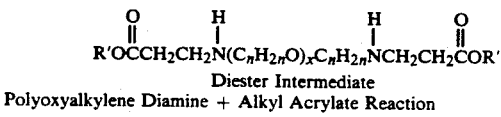

Polyoxyalkylene Diamine + Alkyl Acrylate Reaction

In Equation 1, n and x are as defined in Formula 1 and R' is alkyl.

The alkyl acrylate can have any suitable alkyl substituent, R'. For example, R' can be straight or branched chain, saturated or unsaturated, cyclic or acyclic, unsubstituted or substituted, and have at least 1, preferably from 1 to about 4, and most preferably 1 or 2, carbon atoms. Typical alkyl acrylates include, among others, one or mixtures of the following: methyl acrylate, ethyl acrylate, propyl acrylate, butyl acrylate, methoxyethyl acrylate, and so on. Preferred alkyl acrylates are methyl acrylate and ethyl acrylate.

The polyoxyalkylene diamine can be polyoxyethylene diamine where all n in Equation 1 are 2, polyoxypropylene diamine where all n in Equation 2 are 3, or polyoxyalkylene diamine having mixtures of oxyethylene and oxypropylene where n values in Equation 1 are both 2 and 3. Polyoxyalkylene mixtures may contain random or block repeating units of oxyethylene and oxypropylene in any relative amount. The average number of oxyalkylene repeating units in the polyoxyalkylene diamine, defined by x in Formula 1 and Equation 1, is at least 1, preferably from about 1 to about 60, and most preferably from about 2 to about 6. The weight average molecular weight of the polyoxyalkylene diamine is typically from about 100 to about 2,000, preferably from about 140 to about 400, and most preferably from about 148 to about 192.

Suitable polyoxyalkylene diamines include, among others, one or mixtures of the following: JEFFAMINE ® Polyoxypropylene D-Series or Polyoxyethylene EDR-Series, both from Texaco Chemical Company, Inc., such as D-230, D-400, D-2000, EDR-148, EDR-192, and the like.

The relative amount of acrylate to diamine is any amount sufficient to produce the diester intermediate. Generally, a slight excess of acrylate, i.e. of ethylenic unsaturation, is provided per mole equivalent of amine in the diamine. Preferably, the molar ratio of acrylate to amine is from about 1:1 to about 1.5:1, and most preferably from about 1:1 to about 1.1:1.

The addition reaction between acrylate and diamine may be conducted under any suitable, including known, conditions for reacting amine with ethylenic unsaturation. The reaction temperature may range from about 30° C. to about 120° C., preferably from about 60° C. to about 110° C. The reaction pressure may range from ambient, or less, up to about 100, and preferably is about atmospheric pressure.

TMAP, including N-alkyl substituted TMAP, reacts with the diester intermediate, by a condensation reaction of amine and ester, to make alcohol by-product (R'OH) and amide-containing, TMAP derivative, as shown in Equation 2.

and pressures are similar to those described previously for producing the intermediate.

If desired, other ingredients can be added before, during or after the addition or condensation reactions. Typical additives include, among others, one or mixtures of the following: catalyst; solvent; stabilizer; or other useful materials.

The TMAP derivative of this invention is useful as a photostabilizer. The compound can be added to polymeric or any other light sensitive material which undergoes a change in physical properties due to exposure to light. Light sensitive materials include, among others, one or mixtures of the following: synthetic polymers like polyethylene, polypropylene, polyvinyl chloride, polyurethane, acrylonitrile/butadiene/styrene copolymer, and the like; and other light sensitive materials such as used in paints, coatings or elsewhere.

The amount of TMAP derivative added to such materials is an effective photostabilizing amount, i.e. any amount which is sufficient to reduce any physical Reaction of Intermediate with TMAP

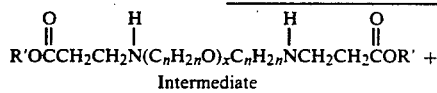

Equation 2.

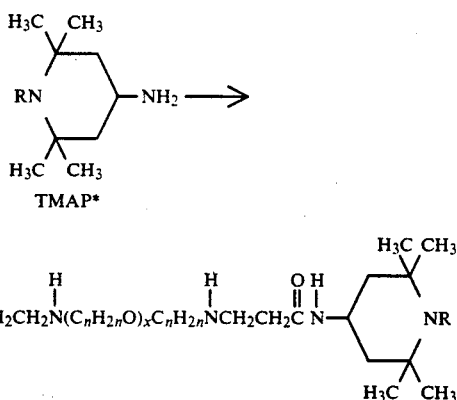

TMAP Derivative
Reaction of Itermediate with TMAP
*including N-substituted compounds The variables in Equation 2, of n, x, R and R', are as defined previously in Formula 1 and Equation 1.

The TMAP starting material, with a structure shown as TMAP* in Equation 2, may be unsubstituted or have a substituent on the piperidyl ring nitrogen atom, designated by R, which is hydrogen for unsubstituted TMAP. The term "TMAP" is used in the specification both to describe either the specific compound 2,2',6,6'-tetramethyl-4-aminopiperidine, or when referring to a class of compounds to describe 2,2',6,6'-tetramethyl-4-aminopiperidine as well as corresponding N-substituted compounds. When other than hydrogen, the nitrogen substituent is generally alkyl, although any other substantial equivalent can be used. Typical hydrocarbyl substituents can be straight or branched chain, saturated or unsaturated, cyclic or acyclic, unsubstituted or substituted, and have at least 1, preferably from 1 to about 16, and most preferably from 1 to about 4, carbon atoms. R is preferably hydrogen.

The amine/ester condensation reaction may be conducted under any suitable, including known, reaction conditions effective for reacting ester with amine to produce amide bonds. Typical reaction temperatures changes due to light exposure. Typically, the amount of TMAP derivative ranges from about 0.035 to about 1, preferably from about 0.05 to about 0.5, and most preferably from about 0.06 to about 0.25, weight percent of the total, usually polymeric, light sensitive material.

Other photostabilizers or ingredients can be added. Typical additives include, among others, one or mixtures of the following: photostabilizers like other TMAP derivatives or materials, such as described in U.S. Pat. No. 4,526,972 (Speranza et al.) and No. 4,847,380 (Speranza et al.), which are both incorporated herein by reference; heat stabilizers; antistatic agents; and any other useful materials.

The following examples present illustrative embodiments of this invention without intention to limit its scope. All percentages given in the disclosure and claims are in weight percent, unless otherwise stated.

EXAMPLES

Terms used in the examples have the following meanings:

| Term | Designation |
| --- | --- |
| D-230 | Polyoxypropylene diamine having a weight average molecular weight of 230, called JEFFAMINE ® D-230 from Texaco Chemical Co. Inc. |
| EDR-148 | Polyoxyethylene diamine, made with triethylene glycol initiator, having a weight average molecular weight of 148, called JEFFAMINE ® EDR-148 from Texaco Chemical Co. Inc. |
| EDR-192 | Polyoxyethylene diamine, made with tetraethylene glycol initiator having a weight average molecular weight of 192, called JEFFAMINE ® EDR-192 from Texaco Chemical Co. Inc. |

EXAMPLE 1

In this example, TMAP derivative of this invention is prepared using the following procedure. A 250-milliliter, 3-necked flask equipped with a thermometer, a Dean-Stark ® trap, a stirrer and nitrogen-line is charged with 100 grams (1.0 mole) ethyl acrylate and 115 grams (0.5 mole) D-230. The mixture is heated to 60°-70° C. for 3 hours and then to 70°-100° C. for over 3 more hours. The resulting diester intermediate is a colorless liquid having an amine content of 5.4 milliequivalents per gram (meq/g) (5.0 meq/g calculated). A portion of this intermediate, 80.4 grams (about 0.2 mole), is added to a 250 milliliter, 3-necked flask followed by the addition of 62.4 grams (0.4 mole) of (unsubstituted) TMAP. The mixture is heated to 180° C. slowly and held at that temperature for about an hour. The recovered product is a light brown liquid having a structure as shown in Formula 2. The presence of amide is confirmed by hydrogen nuclear magnetic resonance analysis.

EXAMPLE 2

Another TMAP derivative of this invention is prepared following the procedure set forth in Example 1 except that the D-230 is replaced with EDR-192. The product has an amine content measured at 8.1 meq/g (6.6 meq/g calculated) and a structure as shown in Formula 3.

Example 2 Product

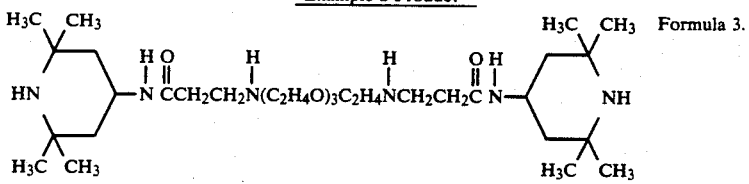

Formula 3.

EXAMPLE 3

Further TMAP derivative of this invention is prepared following the procedure set forth in Example 1 except that the D-230 is replaced with EDR-148. The product has an amine content measured at 8.9 meq/g (7.0 meq/g calculated) and a structure as shown in Formula 4.

Example 3 Product

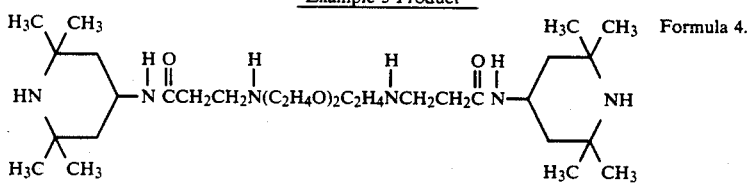

Formula 4.

EXAMPLE 4C (CONTROL)

This example is conducted for comparison. A 250 milliliter, 3-necked flask equipped with a thermometer, a Dean-Stark ® trap, a stirrer and nitrogen-line, is charged with 78 grams (0.5 mole) TMAP and then 21.5 grams (0.25 mole) methyl acrylate. The mixture is slowly heated to 200° C. over a 5 hour period. A soft, solid material is obtained, 84.5 grams, which by hydrogen nuclear magnetic resonance analysis is the di-TMAP adduct of the acrylate, having a structural formula as represented in Formula 5.

Example 4C Product

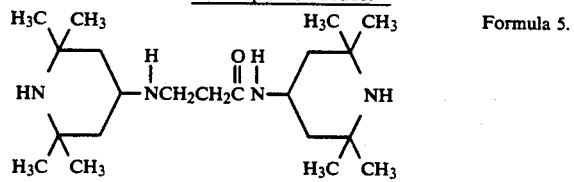

Formula 5.

Example 1 Product

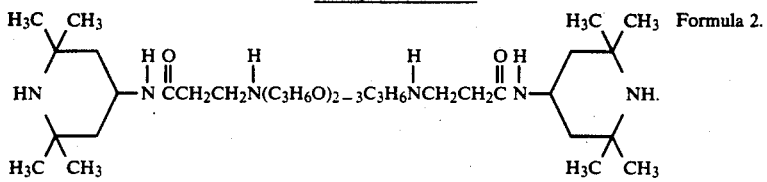

Formula 2.

EXAMPLE 5C (CONTROL)

The procedure in Example 4 is repeated except that the amount of TMAP is reduced to 46.8 grams (0.3 mole) and the methyl acrylate is replaced with 15 grams (0.15 mole) of methyl methacrylate. The mixture is heated slowly to 200° C. and held for a little over an hour. The recovered yellow liquid is analyzed, by hydrogen nuclear magnetic resonance, as only starting material, such that no reaction occurs.

EXAMPLE 6C (CONTROL)

The reaction procedure in Example 5 is repeated except that the methyl methacrylate is replaced with 17.2 grams (0.1 mole) dimethyl maleate and using a reaction temperature of 200° C. The material recovered, 44 grams, is shown by hydrogen nuclear magnetic resonance analysis to have no olefin group remaining. The product is a black colored solid which is believed to have a structure as set forth in Formula 6.

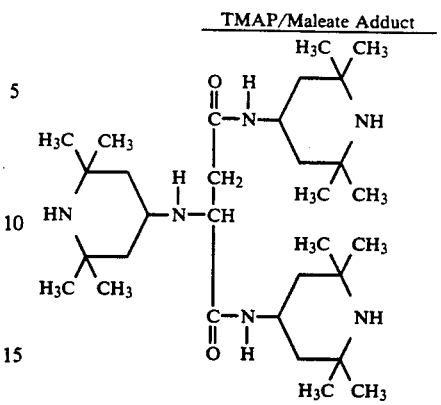

TMAP/Maleate Adduct

Formula 6.

We claim:

1. A photostabilizer represented by the structural formula:

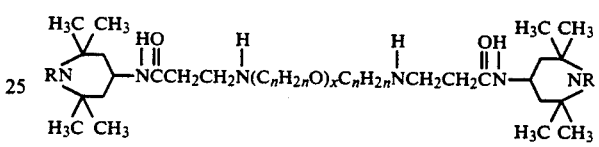

wherein each pair of n per $C_nH_{2n}$ group are 2 or 3, R is hydrogen or hydrocarbyl having from 1 to about 16 carbon atoms and x is from 1 to about 60.

2. The photostabilizer of claim 1 wherein all n are either 2 or 3, R is hydrogen, and x is from about 2 to about 6.

3. A process for producing the photostabilizer of claim 1 by (1) reacting polyoxyalkylene diamine with a molar excess of alkyl acrylate to produce bis(alkylcarboxylatoethyleneamino) polyoxyalkylene intermediate; and (2) reacting the intermediate with a TMAP compound which is unsubstituted or N-hydrocarbyl substituted, 2,2',6,6'-tetramethyl-4-aminopiperidine.

4. The process of claim 3 wherein the polyoxyalkylene diamine is polyoxypropylene or polyoxyethylene diamine having an average of from 1 to about 6 oxyalkylene repeating units, the acrylate is ethyl acrylate, and the TMAP compound is unsubstituted 2,2',6,6'-tetramethyl-4-aminopiperidine.

* * * * *